(12) United States Patent
Arkles et al.

(10) Patent No.: US 8,653,294 B2
(45) Date of Patent: Feb. 18, 2014

(54) SILICONES DERIVED FROM 2-PROPENYL FUNCTIONAL CYCLIC TERPENES AND METHODS OF PREPARATION

(75) Inventors: Barry C. Arkles, Pipersville, PA (US); Rudolph Cameron, Bensalem, PA (US); Youlin Pan, Langhorne, PA (US); Gerald L. Larson, Newton, PA (US)

(73) Assignee: Gelest Technologies, Inc., Morrisville, PA (US)

( * ) Notice: Subject to any disclaimer, the term of this patent is extended or adjusted under 35 U.S.C. 154(b) by 0 days.

(21) Appl. No.: 13/372,964

(22) Filed: Feb. 14, 2012

(65) Prior Publication Data

US 2012/0215019 A1    Aug. 23, 2012

Related U.S. Application Data

(60) Provisional application No. 61/443,943, filed on Feb. 17, 2011.

(51) Int. Cl.
*C07F 7/02* (2006.01)

(52) U.S. Cl.
USPC .......................................................... 556/456

(58) Field of Classification Search
USPC .......................................................... 556/456
See application file for complete search history.

(56) References Cited

PUBLICATIONS

Bažant et al: "Organosilicon Compounds"; vol. 2; Part 1; pp. 117, 493-495; Publishing House of the Czechoslovak Academy of Sciences Prague; Academic Press New York and London (1965).
Valade et al: "Étude des produits d'addition du trichlorosilane au d-limonène"; Bulletin de la Societe Chimique de France; pp. 473-477 (1958).
Tanaka et al: Kogyo Kagaku Zasshi; 716; pp. 923-928 (1968).

*Primary Examiner* — Shawquia Young
(74) *Attorney, Agent, or Firm* — Panitch Schwarze Belisario & Nadel LLP

(57) ABSTRACT

Novel silicone compounds containing a siloxane moiety and at least one terpenyl moiety, such as limonenyl or valencenyl, and methods for their synthesis, are provided. The novel compounds are appropriate for incorporation into cosmetic formulations due to their low aroma, resistance to deterioration, and favorable solubility properties.

15 Claims, No Drawings

SILICONES DERIVED FROM 2-PROPENYL FUNCTIONAL CYCLIC TERPENES AND METHODS OF PREPARATION

CROSS-REFERENCE TO RELATED APPLICATIONS

This application claims the benefit of U.S. provisional patent Application No. 61/443,943, filed Feb. 17, 2011, the disclosure of which is incorporated herein by reference.

BACKGROUND OF THE INVENTION

Terpenes are organic compounds which may be found in nature or prepared synthetically. Terpenes are derived from isoprene, and may involve cyclic compounds, such as limonene (obtainable from lemon rinds) and valencene (which may be obtained from Valencia oranges), having the structures shown below.

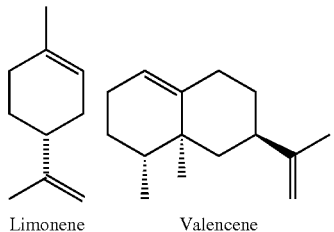

Limonene    Valencene

These terpenes have pleasant citrus fragrances; d-limonene is used in cosmetics, food and drug manufacturing, and in environmentally friendly cleaning products.

BRIEF SUMMARY OF THE INVENTION

Silicone compounds according to the present invention comprise a siloxane moiety and at least one terpenyl moiety, wherein the at least one terpenyl moiety is derived from a cyclic terpene compound comprising an acyclic 2-propenyl group.

A method for preparing the silicone compounds comprising a siloxane moiety and at least one terpenyl moiety, according to one embodiment of the invention comprises preparing a terpenylmethyldichlorosilane and performing a hydrolysis-polymerization reaction on the terpenylmethyldichlorosilane to yield the corresponding silicone compound.

A method for preparing the silicone compounds comprising a siloxane moiety and at least one terpenyl moiety, according to a second embodiment of the invention comprises hydrosilylating a hydride functional siloxane with at least one terpene compound.

DETAILED DESCRIPTION OF THE INVENTION

This invention is directed to siloxane derivatives (silicones) of terpene, particularly limonene and valencene, and methods for their preparation. These silicones are useful for various applications, including formulation into personal care products. The silicones according to the invention are unique hybrid organosilicon compounds formed by attaching the terpene to a siloxane backbone. The terpene substituent adds biocompatibility to the siloxane backbone, whereas the siloxane component improves the slip and skin feel of the terpene. This unique structure enables the organosilicon compounds to act as a solvent for a number of mineral and vegetable waxes and oils.

For the purposes of this disclosure, the term "terpene" is intended to be limited to cyclic terpenes having acyclic unsaturation, preferably terpenes containing 2-propenyl groups, such as limonene and valencene.

The siloxane-based terpenes (silicones) according to the invention comprise a siloxane moiety and at least one terpenyl moiety, which is derived from a cyclic terpene compound comprising an acyclic 2-propenyl group, such as limonene or valencene in preferred embodiments. Preferably, the siloxane moiety is bound to the terpenyl moiety through the acyclic 2-propenyl group. Exemplary compounds according to the invention (with simplified names) include:

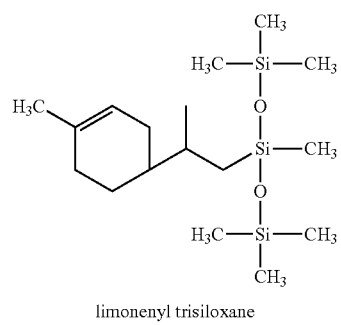

limonenyl trisiloxane

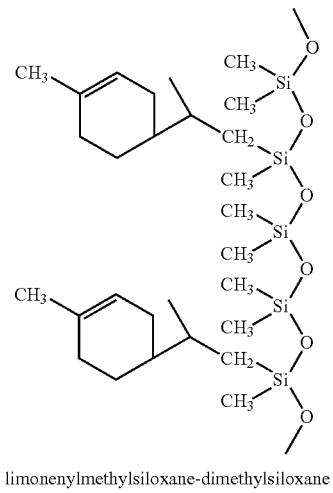

limonenylmethylsiloxane-dimethylsiloxane copolymer

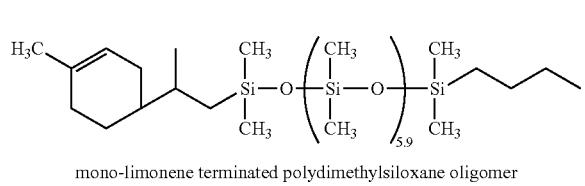

mono-limonene terminated polydimethylsiloxane oligomer

-continued

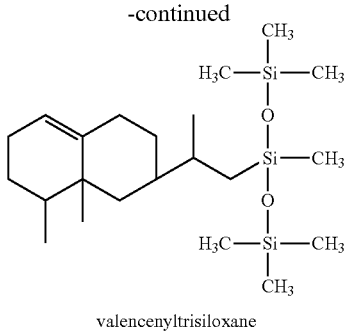

valencenyltrisiloxane

Preferred siloxanes contain about 3 to about 1000 silicon atoms, more preferably about 3 to about 18 silicon atoms, even more preferably about 3 to about 10 silicon atoms, thus encompassing short chain siloxanes, which are often referred to as oligosiloxanes, and longer polysiloxanes. The siloxanes preferably contain alkyl substituents (linear or branched containing up to about 18 carbon atoms), including methyl substituents, such as polydimethylsiloxanes and oligodimethylsiloxanes, and may also be copolymers, yielding silicones such as limonenylmethylsiloxane-dimethylsiloxanes. Other preferred siloxanes are terpolymers, such as terpenylmethylsiloxane-alkylmethylsiloxane-dimethylsiloxane terpolymers in which linear or branched alkanes up to about 18 carbons are preferred, and terpenylmethylsiloxane-arylalkylmethylsiloxane-dimethylsiloxane terpolymers, in which arylalkyl substituents such as 2-phenylethyl or 2-phenylpropyl derived from styrene and alpha-methylstyrene are preferred. It is within the scope of the invention for the terpenyl moiety to occupy a terminal or pendant position on the siloxane, which may have a linear or branched backbone structure.

Other preferred embodiments of the invention include trisiloxanyl and low molecular weight linear siloxane derivatives of limonene or valencene, in which one silicon-based group is bound through a 2-propenyl group to one limonene or valencene molecule. The invention also includes derivatives in which one silicon-based group is attached to multiple terpene molecules through their 2-propenyl groups. Thus, silicone compounds containing multiple terpenyl moieties, which may be the same or different, are within the scope of the invention.

Specific preferred compounds according to the invention include, for example, limonenyl trisiloxane, limonenylmethylsiloxane-dimethylsiloxane copolymer, mono-limonene terminated polydimethylsiloxane oligomer, valencenyltrisiloxane, alpha-butyl-omega-limonenyl terminated polydimethylsiloxane oligomer, and limonenyltris(trimethylsiloxy)silane/limonenyltrimethicone.

Several different synthetic approaches may be used to prepare the silicone compounds according to the invention. For example, they may be prepared via reaction (hydrosilylation) of a hydride functional siloxane with the appropriate terpene to form a hydrolytically stable silicon-to-carbon bond. Such reactions, including appropriate catalysts, solvents, and reaction conditions, are well known in the art.

Alternatively, the compounds may be prepared by a hydrolysis-polymerization reaction of a terpenylmethyldichlorosilane (prepared, for example, by the method of R. Tanaka, *Kogyo Kagaku Zasshi*, 716: 923-8 (1968). In such a method, which is well known in the art, two electronegative groups or atoms attached to silicon are displaced by the reaction of water to firm, initially, a disilanol which condenses in a catalyzed or heat driven reaction to form a polysiloxane. It is also possible to utilize an end-capping reaction with silanol or a silanolate functional siloxane. In such a reaction, a silanol terminated polydimethylsiloxane is reacted with a compound such as limonenenyldimethyldimethylaminosilane to form an alpha omega limonenyl terminated polydimethylsiloxane. Appropriate reaction conditions for such synthetic methods are well known in the art.

The compounds according to the invention have a broad range of solubility in and compatibility with materials typically used in the formulation of skin care and color cosmetics. Accordingly, the invention is also directed to cosmetic formulations, such as lipsticks and foundations, containing a cleansing emollient, in which the cleansing emollient contains a silicone compound as described herein.

Unexpectedly, the novel terpenyl-siloxane derivatives according to the invention have little or no aroma, in contrast to the unmodified terpenes. They have the additional advantage of being more resistant to becoming rancid or colored during formulation. Unlike many silicones and silicone derivatives, these compounds are easily incorporated into cosmetic products, such as skin-care and color cosmetics, including lipsticks and foundations, due to their solubility in a range of polar compounds, such as castor oil and a variety of cosmetic esters. They can also act as co-solvents for terpenes and silicones. Further, due to this solubility, such derivatives can be useful to enhance the compatibility of bioactives, limonenes, and silicones, among other possible applications. Low molecular weight siloxanes containing a high proportion of limonene functionality, most preferably linear siloxanes, also manifest themselves in compatibility with a variety of natural oils and resins

EXAMPLES

The invention may be further understood in conjunction with the following, non-limiting examples.

Example 1

Preparation of 3-Limonenylheptamethyltrisiloxane (Limonenyltrisiloxane)

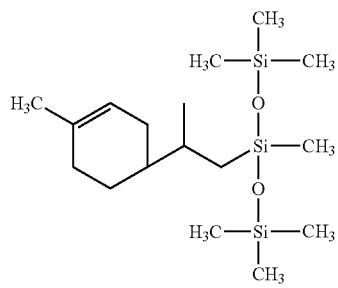

A 3 liter 3-neck flask equipped with a heating mantle, magnetic stirrer, pot thermometer, addition funnel, and condenser was charged with 3.2 moles (433.2 g) of d-limonene and heated to 90-120° C. A 20 g portion of heptamethyltrisiloxane from a total of 3.3 moles (743 g) was added along with 0.5 ml of 2 wt % Pt in the form of Karstedt catalyst. After a few minutes, an exotherm was observed, heating was stopped, and the balance of the heptamethyltrisiloxane was added at an appropriate rate to maintain the pot temperature between 90-120° C. After the addition was completed, the pot temperature was maintained at 100-120° C. for 10-16 hours.

Gas-chromatographic analysis indicated the reaction was complete and the formation of product with >95% isomeric purity. The product was distilled at 132-4° C. under 3 mm Hg vacuum. The final product had a density (20° C.) of 0.879, a refractive index (25° C.) of 1.4404, and a viscosity (25° C.) of 4.5 cSt.

Example 2

Preparation of Limonenylmethylsiloxane-dimethylsiloxane copolymer

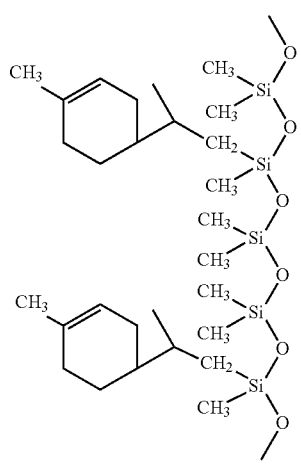 [SMILES: CO[Si](C)(C)O[Si](C)(CC(C)C1CC=C(C)CC1)O[Si](C)(C)O[Si](C)(C)O[Si](C)(CC(C)C1CC=C(C)CC1)OC]

A 5 liter 4-neck flask equipped with a heating mantle, mechanical stirrer, pot thermometer, addition funnel, and condenser was charged with 1308 g of d-limonene and heated to 105-110° C. A 20 g portion from a total of 1950 g of 30% methylhydrogensiloxane-70% dimethylsiloxane was added along with 0.5 ml of 2 wt % Pt in the form of Karstedt catalyst. After an exotherm was observed, heating was halted and the balance of the copolymer was added at an appropriate rate to maintain temperature between 105° C. and 115° C. The reaction was monitored by FTIR to track the consumption of d-limonene, as measured by the disappearance of the 1640 cm$^{-1}$ peak. The mixture was stripped at 160° C. under a vacuum of 10 mm Hg, and the product was filtered through silica. The final product viscosity (25° C.) was 260 cSt, density (20° C.) was 0.98, and refractive index (25° C.) was 1.446.

Example 3

Preparation of alpha-butyl, omega-limonenyl terminated polydimethylsiloxane oligomer

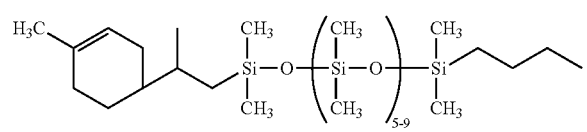

A 1 liter 3-neck flask equipped with a heating mantle, magnetic stirrer, pot thermometer, addition funnel, and condenser was charged with 1.0 M of alpha-butyl omega-hydrido terminated polydimethylsiloxane oligomer having an average DP of 6 that contained <10% di-n-butyl terminated oligomer, and heated to 85° C. 1.2 moles (163.5 g) of d-limonene was charged to an addition funnel. 5-10% of the d-limonene was added along with 0.5 ml of 2 wt % Pt in the form of Karstedt catalyst. After a few minutes, an exotherm was observed, heating was stopped, and the balance of the d-limonene was added at an appropriate rate to maintain the pot temperature between 85° C. and 105° C. After the addition was completed, the pot temperature was maintained at between 95° C. and 110° C. for about 1 hour. Gas-chromatographic analysis indicated that the reaction was complete and the formation of product with >95% isomeric purity. The product was stripped at 160° C. under 10 mm Hg vacuum. The product had a density (20° C.) of 0.92 and a viscosity (25° C.) of 7-8 cSt.

Example 4

Preparation of Limonenyltris(trimethylsiloxy)silane/ Limonenyltrimethicone mixture

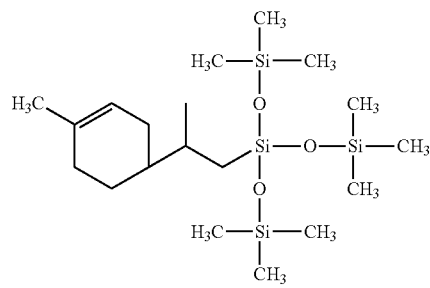

D-limonene was hydrosilylated with trichlorosilane to form a mixture of limonenyltrichlorosilane and isomeric products. The intermediate mixture (749 g) was co-hydrolyzed with 6 moles of trimethylchlorosilane (782 g) by slowly adding a mixture of the chlorosilanes to 3750 g of water. The acidic aqueous layer was separated. The organic layer was washed with 2.5 liters water, with 2.5 liters of 5% sodium bicarbonate in water, and then with 0.5 liters of water. Hexamethyldisiloxane was removed from the mixture under vacuum. The main product fraction was collected at 140-150° C. under 4 mm Hg vacuum. The product had a density (20° C.) of 0.89, a refractive index (25° C.) of 1.4321, and a viscosity (25° C.) of 11 cSt. The product contained a mixture of mainly (approximately 95%) limonenyltris(trimethylsiloxy) silane monomer and approximately 5% of limonenyltrimethicone oligomer.

Example 5

Preparation of Bath Oil Base Formula

A mixture of 80% white mineral oil, 8.0% isopropyl myristate, 6.0% oleth-2, and 6% limonenyltrisiloxane (as prepared according to Example 1) are combined. Fragrance may be added. The formulation is water dispersible and provides a light, silky after feel. Alternate compositions may utilize blends of octyltrimethicone and limonenyltrimethicone to replace the limonenyltrisiloxane.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A silicone compound comprising a siloxane moiety and at least one terpenyl moiety, wherein the at least one terpenyl moiety is derived from a terpene compound selected from the group consisting of limonene and valencene, and wherein the siloxane moiety is selected from the group consisting of siloxane oligomers, siloxane homopolymers, and siloxane copolymers.

2. The compound according to claim 1, wherein the siloxane moiety comprises about 3 to about 1000 silicon atoms.

3. The compound according to claim 1, wherein the siloxane moiety comprises alkyl substituents.

4. The compound according to claim 3, wherein the siloxane moiety comprises methyl substituents.

5. The compound according to claim 1, wherein the at least one terpenyl moiety occupies a terminal or pendant position in the silicone compound.

6. The compound according to claim 1, wherein the siloxane moiety is bonded to the at least one terpenyl moiety through a 2-propenyl group.

7. The compound according to claim 1, wherein the silicone compound is limonenyl trisiloxane.

8. The compound according to claim 1, wherein the silicone compound is limonenylmethylsiloxane-dimethylsiloxane copolymer.

9. The compound according to claim 1, wherein the silicone compound is mono-limonene terminated polydimethylsiloxane oligomer.

10. The compound according to claim 1, wherein the silicone compound is valencenyltrisiloxane.

11. The compound according to claim 1, wherein the silicone compound is alpha-butyl-omega-limonenyl-terminated polydimethylsiloxane oligomer.

12. The compound according to claim 1, wherein the silicone compound is a mixture of limonenyltris(trimethylsiloxy)silane monomer and limonenyltrimethicone oligomer.

13. A cosmetic formulation comprising a cleansing emollient, wherein the emollient comprises a silicone compound according to claim 1.

14. A method for preparing a silicone compound comprising a siloxane moiety and at least one terpenyl moiety, wherein the at least one terpenyl moiety is derived from a terpene compound selected from the group consisting of limonene and valencene, and wherein the siloxane moiety is selected from the group consisting of siloxane oligomers, siloxane homopolymers, and siloxane copolymers, the method comprising preparing a terpenylmethyldichlorosilane and performing a hydrolysis-polymerization reaction on the terpenylmethyldichlorosilane to yield the corresponding silicone compound.

15. A method for preparing a silicone compound comprising a siloxane moiety and at least one terpenyl moiety, wherein the at least one terpenyl moiety is derived from a terpene compound selected from the group consisting of limonene and valencene, and wherein the siloxane moiety is selected from the group consisting of siloxane oligomers, siloxane homopolymers, and siloxane copolymers, the method comprising hydrosilylating a hydride functional siloxane with at least one terpene compound.

* * * * *